(12) United States Patent
Wang et al.

(10) Patent No.: US 7,434,996 B2
(45) Date of Patent: Oct. 14, 2008

(54) METHOD AND APPARATUS FOR A C-ARM SYSTEM

(75) Inventors: Zonghua Wang, Fruit Heights, UT (US); Arvidas Bronislavovich Cheryauka, Salt Lake City, UT (US)

(73) Assignee: General Electric Co., Schenectady, NY (US)

( * ) Notice: Subject to any disclaimer, the term of this patent is extended or adjusted under 35 U.S.C. 154(b) by 8 days.

(21) Appl. No.: 11/624,802

(22) Filed: Jan. 19, 2007

(65) Prior Publication Data
US 2008/0175354 A1     Jul. 24, 2008

(51) Int. Cl.
*H05G 1/02* (2006.01)
(52) U.S. Cl. ................................ 378/197; 378/193
(58) Field of Classification Search .............. 378/193, 378/196, 197
See application file for complete search history.

(56) References Cited

U.S. PATENT DOCUMENTS

| | | | |
|---|---|---|---|
| 5,515,416 A | 5/1996 | Siczek et al. | |
| 6,428,206 B1 * | 8/2002 | Watanabe | 378/197 |
| 6,619,840 B2 * | 9/2003 | Rasche et al. | 378/197 |
| 6,789,941 B1 * | 9/2004 | Grady | 378/197 |
| 6,866,418 B2 | 3/2005 | Pillai et al. | |
| 6,940,941 B2 | 9/2005 | Gregerson et al. | |
| 7,001,045 B2 | 2/2006 | Gregerson et al. | |
| 7,106,825 B2 | 9/2006 | Gregerson et al. | |
| 2004/0013225 A1 | 1/2004 | Gregerson et al. | |
| 2004/0013239 A1 | 1/2004 | Gregerson et al. | |
| 2004/0170254 A1 | 9/2004 | Gregerson et al. | |

* cited by examiner

*Primary Examiner*—Jurie Yun

(57) ABSTRACT

A C-arm system is disclosed herein. The C-arm system includes a support assembly, and a C-extension connected to the support assembly. The C-extension is selectively rotatable relative to the support assembly in both a clockwise and a counterclockwise direction. The C-arm system also includes a C-gantry connected to the C-extension. The C-gantry is adapted to retain an x-ray source and an x-ray detector. The C-gantry is selectively rotatable relative to the C-extension in both a clockwise and a counterclockwise direction. The C-extension is operable to extend the range of C-gantry rotation in both clockwise and counter clockwise directions. A corresponding method for operating a C-arm system is also provided.

18 Claims, 3 Drawing Sheets

METHOD AND APPARATUS FOR A C-ARM SYSTEM

FIELD OF THE INVENTION

This disclosure relates generally to a method and apparatus for a C-arm system having an extendable range of motion.

BACKGROUND OF THE INVENTION

C-arm equipment is commonly implemented for purposes such as surgical planning, co-registration, image fusion, navigation, implant fitting, surgical validation, etc. During these procedures, it is frequently desirable to observe the patient from several different orientations and is often preferable to do so without the need to reposition the patient. C-arm systems have been developed to meet these needs and are now well known in the medical and surgical arts. C-arm systems can be small enough and mobile enough to be present in an operating or exam situation without requiring the physician or technician to repeatedly move and without requiring the patient to change positions to obtain a suitable image. As an example, a gap defined by the C-arm gantry allows the device to laterally access a patient such that patient images are obtainable without physically moving the patient.

An x-ray source and an x-ray detector are generally mounted on opposing ends of the C-arm gantry such that x-rays emitted by the source are incident on and detectable by the x-ray detector. The source and the detector are positioned such that when an object (e.g., a human extremity) is interposed therebetween and is irradiated with x-rays, the detector produces data representative of characteristics of the interposed object. The data produced is frequently displayed on a monitor or electronically stored.

The C-arm gantry defines an axis of rotation about which the source and detector are rotatable. By positioning this axis of rotation at or near an object, and by rotating the source and detector around the object in an orbital motion, images of the object taken at a plurality of different orientations can be obtained. These images can be combined to generate a comprehensive three-dimensional image of the object. The process of combining images to produce a comprehensive three-dimensional image is commonly performed with reconstructive software.

The term "redundancy" refers to the process of obtaining data that is representative of a single portion of an object from multiple different orientations. Increasing the degree of data redundancy correspondingly increases image quality by reducing artifacts. "Artifacts" are distortions in an image that may be generated, for example, by reconstructive software in response to insufficient input data. One problem with conventional C-arm systems is that the gap defined by the C-arm gantry limits the range of orbital motion of the x-ray source and the x-ray detector. This limitation on the range of orbital motion correspondingly limits the degree of data redundancy obtainable, and therefore also limits image quality by increasing artifacts.

BRIEF DESCRIPTION OF THE INVENTION

The above-mentioned shortcomings, disadvantages and problems are addressed herein which will be understood by reading and understanding the following specification.

In an embodiment, a C-arm system includes a support assembly, and a C-extension connected to the support assembly. The C-extension is selectively rotatable relative to the support assembly in both a clockwise and a counterclockwise direction. The C-arm system also includes a C-gantry connected to the C-extension. The C-gantry is adapted to retain an x-ray source and an x-ray detector. The C-gantry is selectively rotatable relative to the C-extension in both a clockwise and a counterclockwise direction. The C-extension is operable to extend the range of C-gantry rotation in both clockwise and counter clockwise directions.

In another embodiment, a C-arm system includes a support assembly defining a support assembly groove, and a C-extension having a first ridge and a second ridge. The C-extension is connected to the support assembly such that the first ridge is disposed at least partially within the support assembly groove. The C-extension is selectively rotatable relative to the support assembly in both clockwise and counterclockwise directions. The C-arm system also includes a C-gantry defining a gantry groove. The C-gantry is connected to the C-extension such that the second ridge is disposed at least partially within the gantry groove. The C-gantry is adapted to retain an x-ray source and an x-ray detector. The C-gantry is selectively rotatable relative to the C-extension in both clockwise and counterclockwise directions. The C-system also includes a first motor operatively connected to the C-extension, a second motor operatively connected to the C-gantry, and a controller operatively connected to the first and second motors such that C-extension rotation and C-gantry rotation can be independently induced in a selectable manner. The C-extension is operable to extend the range of C-gantry rotation in both clockwise and counter clockwise directions.

In another embodiment, a method for operating a C-arm system includes providing a C-extension that is selectively rotatable in a clockwise or counter clockwise direction, and providing a C-gantry that is connected to the C-extension. The C-gantry is selectively rotatable in a clockwise or counter clockwise direction. The method for operating a C-arm system also includes controlling a first motor operatively connected to the C-extension in order to induce a selectable amount of C-extension rotation, and controlling a second motor operatively connected to the C-gantry in order to induce a selectable amount of C-gantry rotation. Independently controlling the first motor and the second motor increases the C-gantry range of rotation in both the clockwise direction and the counter clockwise direction.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
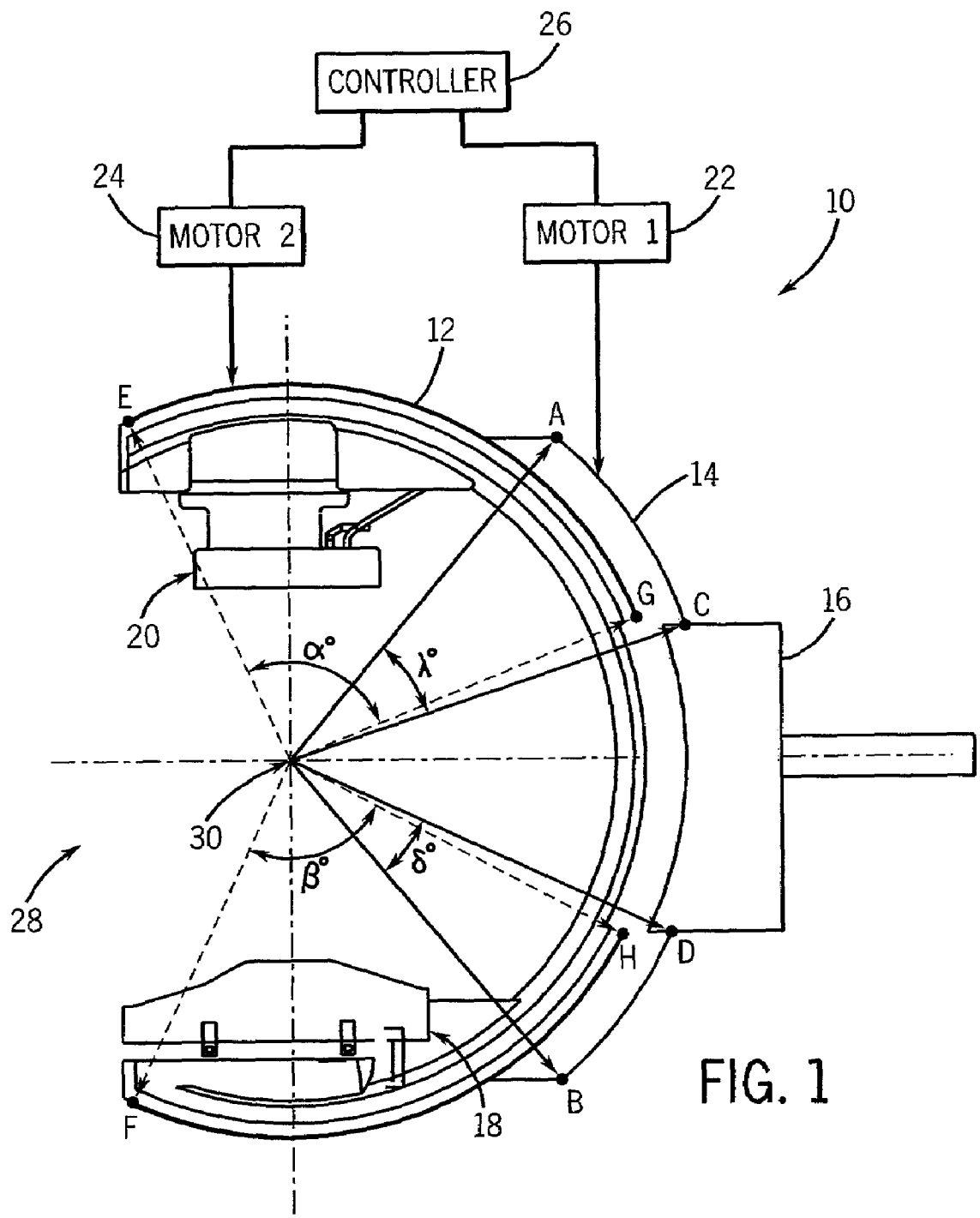
FIG. 1 is a schematic diagram illustrating a C-arm system in accordance with an embodiment.

Referring to FIG. 1, a C-arm system 10 is shown in the home position in accordance with an embodiment. The term "C-arm" generally refers to the shape of a conventional C-arm gantry (sometimes referred to as the C-gantry), however, it should be appreciated that, for purposes of this disclosure, terms such as C-arm, C-gantry and C-extension may encompass other shapes and orientations. The "home position" is that shown in FIG. 1 wherein the x-ray source 18 is at the bottom most or six o'clock position and the x-ray detector 20 is at the upper most or twelve o'clock position.

The C-arm system 10 includes a C-arm gantry or C-gantry 12, a C-arm extension or C-extension 14, and a support assembly 16. The support assembly 16 rotatably supports the C-extension 14 and/or the C-gantry 12 while remaining stationary relative thereto. The C-gantry 12 and the C-extension 14 are independently rotatable. The x-ray source 18 and the x-ray detector 20 are rigidly attached to opposing end portions of the C-gantry 12 such that these components are collectively rotatable as a single unit. The x-ray source 18 emits x-rays (not shown) that are detectable by the x-ray detector 20. The x-ray source 18 and the x-ray detector 20 are configured such that when an object is interposed therebetween and is irradiated with x-rays, the x-ray detector 20 produces data representative of characteristics of the interposed object. This representative data can be implemented in a known manner to generate an image of the interposed object.

For illustrative purposes, this disclosure will hereinafter be described in accordance with an embodiment wherein C-extension 14 rotation is induced by a first motor 22 operatively connected thereto, and C-gantry 12 rotation is induced by a second motor 24 operatively connected thereto. It should be appreciated, however, that C-gantry 12 and C-extension 14 rotation may be induced in any known manner such as, for example, by a single motor operatively connected to both components, or by other types of power sources. A controller 26 is operatively connected to both the first and second motors 22, 24. The controller 26 is adapted to operate one or both of the first and second motors 22, 24 and thereby selectively rotate the C-gantry 12 and/or the C-extension 14 as will be described in detail hereinafter.

The C-gantry 12 defines a gap 28 and an axis of rotation 30. The C-arm system 10 is configured to laterally access a stationary object (not shown) such as a human patient. More precisely, the gap 28 accommodates the stationary object as the C-arm system 10 is translated into position such that the axis of rotation 30 generally coincides with the object's region of interest (e.g., a human extremity). Thereafter, the x-ray source 18 and the x-ray detector 20 are rotatable around the axis of rotation 30 to obtain a comprehensive three-dimensional image of the region of interest.

Reference point A identifies a first terminal end of the C-extension 14, and reference point B identifies a second terminal end of the C-extension 14. Reference point A of the C-extension 14 is rotatable in a clockwise direction from the home position shown in FIG. 1 to the position labeled reference point C. Therefore, the range of C-extension 14 rotation in the clockwise direction is defined by $\lambda$ which is the angular displacement between reference points A and C. Reference point B of the C-extension 14 is rotatable in a counter clockwise direction from the home position shown in FIG. 1 to the position labeled reference point D. Therefore, a maximum range of C-extension 14 rotation in the counter clockwise direction is defined by $\delta$ which is the angular displacement between reference points B and D.

Reference point E identifies a first terminal end of the C-gantry 12, and reference point F identifies a second terminal end of the C-gantry 12. Reference point E of the C-gantry 12 is rotatable in a clockwise direction from the home position shown in FIG. 1 to the position labeled reference point G. If the C-extension 14 is held stationary, the range of C-gantry 12 rotation in the clockwise direction is defined by $\alpha$ which is the angular displacement between reference points E and G. Reference point F of the C-gantry 12 is rotatable in a counter clockwise direction from the home position shown in FIG. 1 to the position labeled by reference point H. If the C-extension 14 is held stationary, the range of C-gantry 12 rotation in the counter clockwise direction is defined by $\beta$ which is the angular displacement between reference points F and H.

Figure 2:
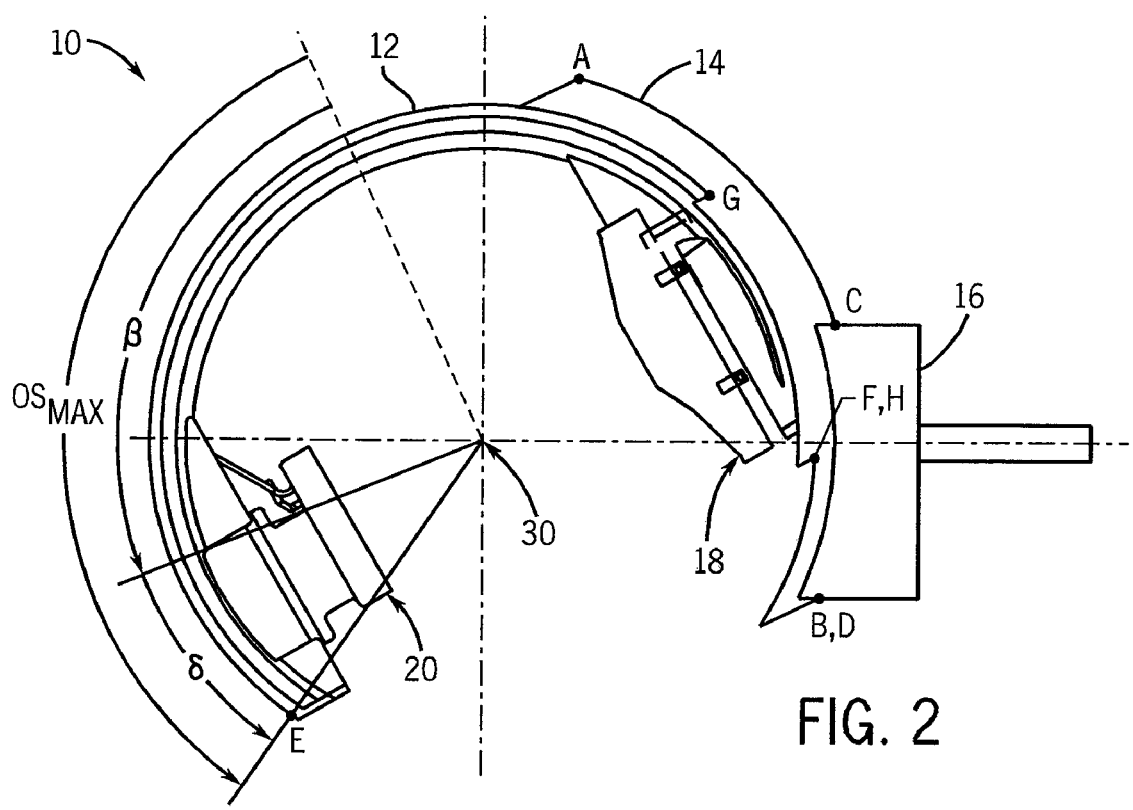
FIG. 2 is a schematic diagram illustrating the C-arm system of FIG. 1 rotated to the over scan end limit.

Referring to FIG. 2, the C-arm system 10 is shown with the C-gantry 12 rotated to the over scan end limit ($OS_{max}$). For purposes of this disclosure, "over scan" is defined as the degree to which reference point E identifying a terminal end of the C-gantry 12 is rotated in the counter clockwise direction from its home position shown in FIG. 1. As previously indicated, if the C-extension 14 is held stationary, C-gantry 12 over scan is limited to $\beta°$ of rotation. If, however, the C-extension 14 is rotated by its maximum counter clockwise amount $\delta°$, the allowable C-gantry 12 over scan $OS_{max}$ becomes $(\beta+\delta)°$ of rotation. Therefore, the implementation of the C-extension 14 increases the maximum C-gantry over scan $OS_{max}$ by $\delta°$. This increase in C-Gantry 12 over scan range also increases the maximum allowable degree of data redundancy which correspondingly increases x-ray image quality by reducing artifacts.

Figure 3:
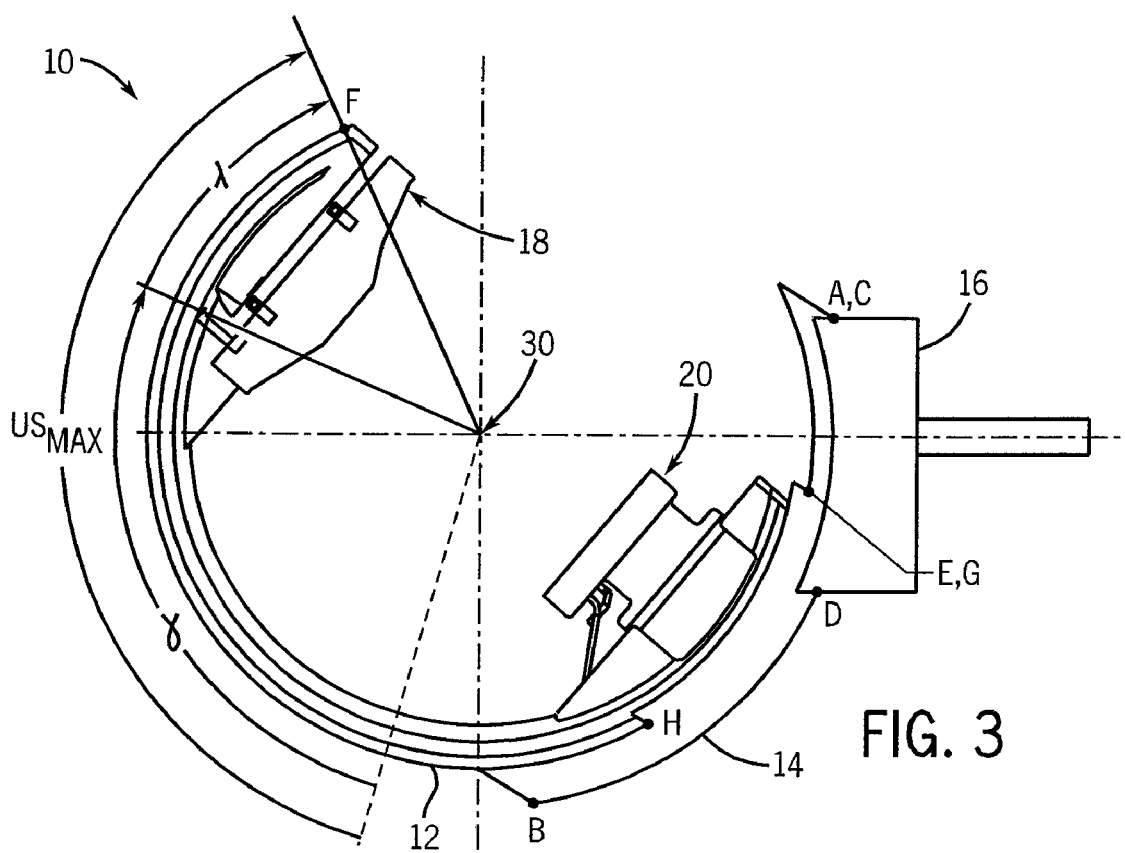
FIG. 3 is a schematic sectional diagram illustrating the C-arm system of FIG. 1 rotated to the under scan end limit.

Referring to FIG. 3, the C-arm system 10 is shown with the C-gantry 12 rotated to the under scan end limit ($US_{max}$). For purposes of this disclosure, "under scan" is defined as the degree to which reference point F identifying a terminal end of the C-gantry 12 is rotated in the clockwise direction from its home position shown in FIG. 1. As previously indicated, if the C-extension 14 is held stationary, C-gantry 12 under scan is limited to $\alpha°$ of rotation. If, however, the C-extension 14 is rotated by the maximum clockwise amount $\lambda°$, the allowable C-gantry 12 under scan $US_{max}$ becomes $(\alpha+\lambda)°$ of rotation. Therefore, the implementation of the C-extension 14 increases the maximum C-gantry under scan $US_{max}$ by $\lambda°$. This increase in C-Gantry 12 under scan range also increases the maximum allowable degree of data redundancy which correspondingly increases x-ray image quality by reducing artifacts.

Advantageously, the C-extension 14 can extend the total range of C-gantry 12 rotation to 360° allowing for optimal x-ray image quality. As an example, a C-arm system has been developed wherein the reference characters $\alpha$, $\beta$, $\lambda$ and $\delta$ have approximate values of 95°, 110°, 75°, and 80°, respectively. Therefore, according to the exemplary embodiment, the maximum over scan $OS_{max}$ previously defined as $(\beta+\delta)°$ is 190°, and the maximum under scan $US_{max}$ previously defined as $(\alpha+\lambda)°$ is 170°. Total C-gantry 12 rotation, which is equal to the sum of the maximum over scan and the maximum under scan ($OS_{max}+US_{max}$), is therefore 360°. The full 360° scan range of the exemplary C-arm system provides significantly greater x-ray image quality than conventional C-arm systems which have only 200°-220° of total rotation.

Figure 4:
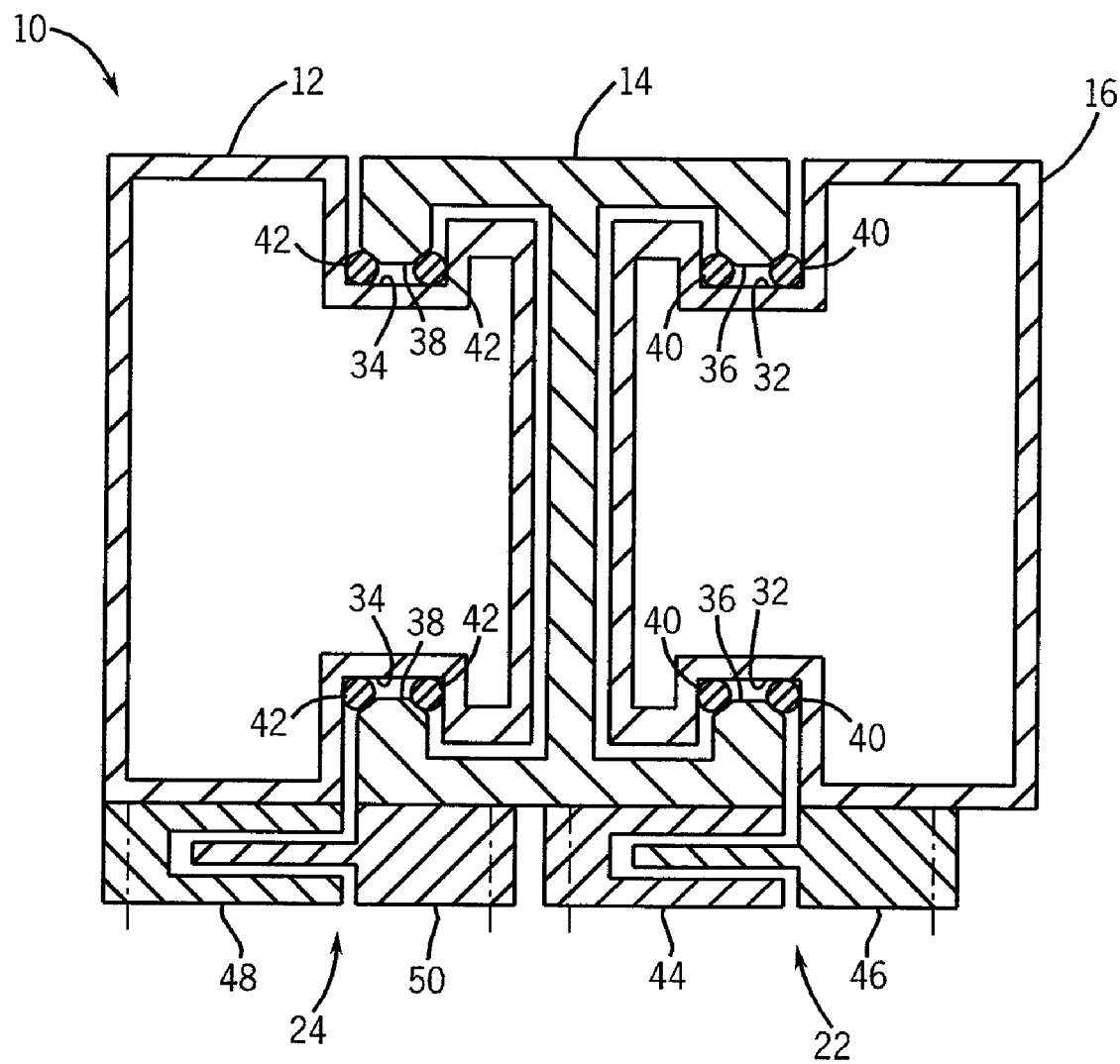
FIG. 4 is a cross-sectional diagram illustrating the C-arm system of FIG. 1 in accordance with an embodiment.

The C-arm system 10 will hereinafter be described in accordance with an exemplary embodiment wherein the first and second motors 22, 24 (shown in FIG. 1) are arc-shaped linear motors. As is known in the art, a "linear motor" is a type of electric motor configured to produce linear rather than rotational output. The arc-shape of the exemplary linear motors therefore produce generally linear output along the arc defining their shape. Referring now to FIG. 4, a cross sectional diagram illustrates the motors 22, 24 attached to the C-gantry 12, the C-extension 14, and the support assembly 16 in accordance with an exemplary embodiment. It should be appreciated that other motor configurations, and other C-gantry 12, C-extension 14, and support assembly 16 sectional configurations may alternatively be envisioned.

The support assembly 16 cross-section is generally rectangular and defines a reduced diameter portion referred to herein as the support assembly groove 32. The C-gantry 12 cross-section is also generally rectangular and defines a reduced diameter portion referred to herein as the gantry groove 34. The C-extension 14 cross-section is generally I-shaped, and is preferably positioned between and connected to the C-gantry 12 and the support assembly 16. The C-extension 14 includes a first protrusion or ridge 36 that is adapted for engagement with the complementary support assembly groove 32 such that the C-extension 14 is supported by and piloted on the support assembly 16. The C-extension 14 includes a second protrusion or ridge 38 that is adapted for engagement with the complementary gantry groove 34 such that the C-extension 14 is also supported by and piloted on the C-gantry 12. While the cross-sectional geometry of the C-arm system 10 components has been described in accordance with an embodiment wherein adjacent components have complementary interlocking retention features (i.e., a groove and a ridge), it should be appreciated that the specific retention features may vary. As an example, according to one alternate embodiment, the C-extension may include first and second grooves (not shown) respectively engaged by a support assembly ridge (not shown) and a gantry ridge (not shown).

According to one embodiment, a first plurality of bearings 40 are disposed between the support assembly 16 and the C-extension 14 in order to minimize frictional losses caused by relative motion therebetween. More precisely, the first plurality of bearings 40 are disposed within the support assembly groove 32 and are engaged by the ridge 36 of the C-extension 14. A second plurality of bearings 42 may be similarly disposed between the C-gantry 12 and the C-extension 14 in order to minimize frictional losses caused by relative motion therebetween. The bearings 40 and 42 may include any type of bearing devices such as, for example, ball bearings or roller bearings, any may also include any known device adapted to facilitate relative motion and minimize friction.

The arc-shaped linear motor 22 includes a translatable rotor 44 and a stator 46. The rotor 44 of motor 22 is mounted to the C-extension 14, and the stator 46 of motor 22 is mounted to the support assembly 16. The linear motion of the rotor 44 is imparted to the C-extension 14 attached thereto such that the C-extension 14 is translated relative to the support assembly 16. The curved geometry of the C-extension 14 converts this linear motion into rotation about the axis of rotation 30 (shown in FIG. 1). The arc-shaped linear motor 24 includes a translatable rotor 48 and a stator 50. The rotor 48 of motor 24 is mounted to the C-gantry 12, and the stator 50 of motor 24 is mounted to the C-extension 14. The linear motion of the rotor 48 is imparted to the C-gantry 12 attached thereto such that the C-gantry 12 is translated relative to the C-extension 14. The curved geometry of the C-gantry 12 converts this linear motion into rotation about the axis of rotation 30.

For some applications, it may be desirable to maintain relatively constant velocity of the x-ray source 18 and the x-ray detector 20 as they are rotated about the axis of rotation 30 (shown in FIG. 1) on the C-gantry 12. Such constant velocity can be maintained by implementing the controller 26 (shown in FIG. 1) to coordinate the motors 22, 24 in a predefined manner. According to one embodiment, the motors 22, 24 can be operated sequentially such that the first motor 22 is operated to rotate the C-extension 14 in a first direction and at a first speed, and thereafter the second motor 24 is operated to rotate the C-gantry 12 in the first direction and at approximately the first speed. In this manner, the accumulated rotational speed otherwise produced by operating the motors simultaneously can be avoided.

While the invention has been described with reference to preferred embodiments, those skilled in the art will appreciate that certain substitutions, alterations and omissions may be made to the embodiments without departing from the spirit of the invention. Accordingly, the foregoing description is meant to be exemplary only, and should not limit the scope of the invention as set forth in the following claims.

We claim:

1. A C-arm system comprising:
  a support assembly;
  a C-extension connected to the support assembly, said C-extension being selectively rotatable relative to the support assembly in both a clockwise and a counter-clockwise direction; and
  a C-gantry connected directly to the C-extension, said C-gantry adapted to retain an x-ray source and an x-ray detector, said C-gantry being selectively rotatable relative to the C-extension in both a clockwise and a counterclockwise direction;
  wherein the C-extension is operable to extend the range of C-gantry rotation in both a clockwise direction and a counter clockwise direction.

2. The C-arm system of claim 1, wherein the C-extension is configured to extend the range of C-gantry rotation to approximately 360 degrees.

3. The C-arm system of claim 1, further comprising a motor operatively connected to the C-extension and the C-gantry.

4. The C-arm system of claim 3, wherein the motor includes a first electric motor operatively connected to the C-extension and a second electric motor operatively connected to the C-gantry.

5. The C-arm system of claim 4, further comprising a controller operatively connected to the first electric motor and the second electric motor.

6. The C-arm system of claim 4, wherein the first and second electric motors are arc-shaped linear motors.

7. The C-arm system of claim 1, wherein said support assembly and said C-extension include a first set of complementary retention features, and wherein said C-extension and said C-gantry include a second set of complementary retention features.

8. The C-arm system of claim 7, wherein said first set of complementary retention features and said second set of complementary retention features include a groove and a ridge.

9. The C-arm system of claim 8, further comprising a first bearing member disposed between the support assembly and the C-extension, and a second bearing member disposed between the C-extension and the C-gantry.

10. A C-arm system comprising:
  a support assembly defining a support assembly groove;
  a C-extension having a first ridge and a second ridge, said C-extension connected to the support assembly such that the first ridge is disposed at least partially within the support assembly groove, said C-extension being selectively rotatable relative to the support assembly in both a clockwise and a counterclockwise direction;

a C-gantry defining a gantry groove, said C-gantry connected to the C-extension such that the second ridge is disposed at least partially within the gantry groove, said C-gantry adapted to retain an x-ray source and an x-ray detector, said C-gantry being selectively rotatable relative to the C-extension in both a clockwise and a counterclockwise direction;

a first motor operatively connected to the C-extension;

a second motor operatively connected to the C-gantry; and a controller operatively connected to the first motor and the second motor such that C-extension rotation and C-gantry rotation can be independently induced in a selectable manner;

wherein the C-extension is operable to extend the range of C-gantry rotation in both a clockwise direction and a counter clockwise direction.

11. The C-arm system of claim 10, wherein the C-extension is configured to extend the range of C-gantry rotation to approximately 360 degrees.

12. The C-arm system of claim 10, wherein the first and second electric motors are arc-shaped linear motors.

13. The C-arm system of claim 10, further comprising a first bearing member disposed between the support assembly and the C-extension, and a second bearing member disposed between the C-extension and the C-gantry.

14. A method for operating a C-arm system comprising:

providing a C-extension that is selectively rotatable in a clockwise or counter clockwise direction;

providing a C-gantry that is directly connected to the C-extension, said C-gantry being selectively rotatable in a clockwise or counter clockwise direction;

controlling a first motor operatively connected to the C-extension in order to induce a selectable amount of C-extension rotation; and controlling a second motor operatively connected to the C-gantry in order to induce a selectable amount of C-gantry rotation;

wherein independently controlling the first motor and the second motor increases the C-gantry range of rotation in both the clockwise direction and the counter clockwise direction.

15. The method of claim 14, further comprising providing a support assembly adapted to rotatably support the C-extension and/or the C-gantry.

16. The method of claim 15, further comprising providing a first bearing member disposed between the support assembly and the C-extension, and providing a second bearing member disposed between the C-extension and the C-gantry.

17. The method of claim 14, further comprising maintaining a relatively uniform rate of rotation of the C-gantry by coordinating the operation of the first motor and the second motor.

18. The method of claim 14, wherein independently controlling the first motor and the second motor increases the C-gantry range of rotation to approximately 360 degrees.

* * * * *